US010065026B2

(12) United States Patent
Lysgaard et al.

(10) Patent No.: US 10,065,026 B2
(45) Date of Patent: Sep. 4, 2018

(54) HIGH STRENGTH BALLOON WITH ASYMMETRIC STRENGTHENING

(71) Applicant: COOK MEDICAL TECHNOLOGIES LLC, Bloomington, IN (US)

(72) Inventors: Thomas Lysgaard, Solroed Strand (DK); Steen Aggerholm, St. Heddinge (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 137 days.

(21) Appl. No.: 15/093,314

(22) Filed: Apr. 7, 2016

(65) Prior Publication Data

US 2017/0072172 A1 Mar. 16, 2017

(30) Foreign Application Priority Data

Mar. 18, 2015 (GB) .................................. 1504568.5
Mar. 18, 2016 (EP) .................................. 16275045

(51) Int. Cl.
*A61M 29/00* (2006.01)
*A61M 25/10* (2013.01)
(Continued)

(52) U.S. Cl.
CPC ......... *A61M 25/1002* (2013.01); *A61F 2/958* (2013.01); *A61M 25/09* (2013.01);
(Continued)

(58) Field of Classification Search
CPC ...... A61M 2025/1075; A61M 25/1029; A61M 2025/1031; A61M 25/1002;
(Continued)

(56) References Cited

U.S. PATENT DOCUMENTS 5,246,421 A * 9/1993 Saab .................... A61M 25/104
128/898
6,746,425 B1 6/2004 Beckham
(Continued)

FOREIGN PATENT DOCUMENTS

WO WO 2002/30484 A2 4/2002
WO WO 2006/086516 8/2006
WO WO 2014/176422 A1 10/2014

OTHER PUBLICATIONS

Examination Report for GB 1504568.5, dated May 5, 2016.
Extended European Search Report for EP 16275045.9, dated Aug. 22, 2016.
Combined Search and Examination Report in corresponding Great Britain Application No. GB1504568.5 dated Aug. 6, 2015, 7 pages.

*Primary Examiner* — Kathleen Holwerda
*Assistant Examiner* — Christina Lauer
(74) *Attorney, Agent, or Firm* — Brinks Gilson & Lione

(57) ABSTRACT

A medical balloon has a strengthening sleeve formed of circumferential fibres and longitudinal fibres. The circumferential fibres have a greater thickness than the longitudinal fibres and preferably have a greater cross-sectional area or volume. In one embodiment, the circumferential fibres are twice as thick as the longitudinal fibres. The use of thinner longitudinal fibres reduces the thickness of the strengthening sleeve and as a result enables a thinner balloon wall, whilst still retaining the circumferential strength of the balloon. Reduced balloon wall thickness improves the foldability and wrappability of the balloon for deployment purposes, and therefore provides a balloon with a smaller diameter for deployment purposes, with improved trackability through a patient's vasculature.

17 Claims, 2 Drawing Sheets

(51) Int. Cl.
*A61F 2/958* (2013.01)
*A61M 25/09* (2006.01)
*A61M 29/02* (2006.01)
*A61B 17/22* (2006.01)

(52) U.S. Cl.
CPC .......... *A61M 25/10* (2013.01); *A61M 25/104* (2013.01); *A61M 29/02* (2013.01); *A61B 2017/22001* (2013.01); *A61B 2017/22051* (2013.01); *A61M 2025/1075* (2013.01); *A61M 2025/1081* (2013.01); *A61M 2025/1084* (2013.01); *A61M 2025/1086* (2013.01)

(58) Field of Classification Search
CPC ... A61M 2025/1081; A61M 2025/1084; A61F 2/962; A61F 2/958
See application file for complete search history.

(56) References Cited

U.S. PATENT DOCUMENTS

| | | |
|---|---|---|
| 2002/0098307 A1 | 7/2002 | Schwartz et al. |
| 2004/0082965 A1 | 4/2004 | Beckham |
| 2006/0085022 A1 | 4/2006 | Hayes et al. |
| 2007/0219490 A1* | 9/2007 | Pepper .................. A61L 29/085 604/103.13 |
| 2008/0033477 A1 | 2/2008 | Campbell et al. |
| 2010/0318029 A1 | 12/2010 | Pepper et al. |
| 2011/0046654 A1* | 2/2011 | Kuppurathanam ... A61M 25/10 606/198 |
| 2013/0085445 A1 | 4/2013 | Hayes et al. |

* cited by examiner

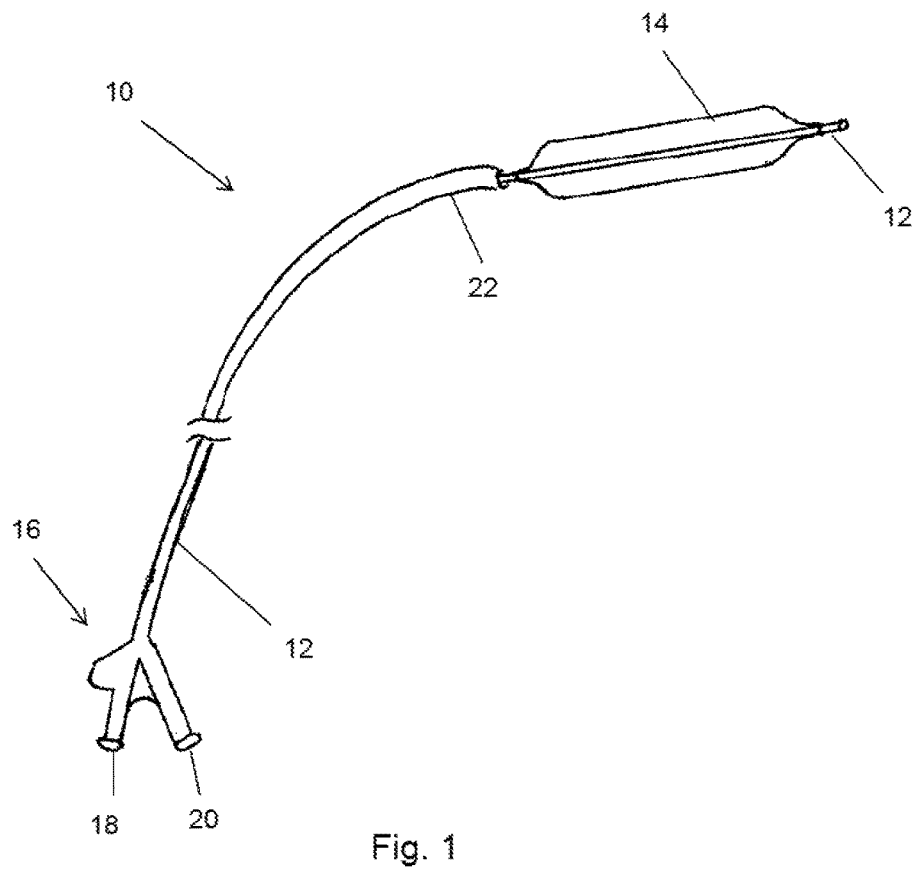
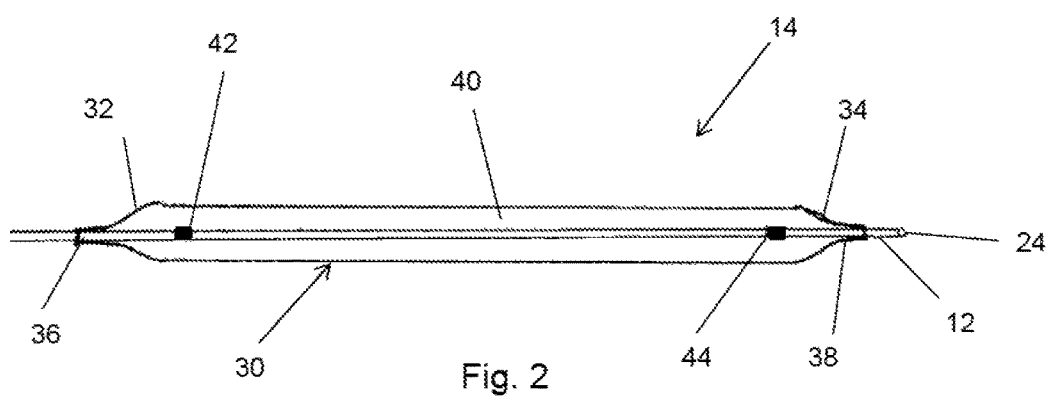

HIGH STRENGTH BALLOON WITH ASYMMETRIC STRENGTHENING

RELATED APPLICATIONS

This application claims the benefit of priority under 35 U.S.C. § 119(a) to European Patent Application No. EP 16275045.9, filed on Mar. 18, 2016, and Great Britain Patent Application No. GB 1504568.5, filed on Mar. 18, 2015, both of which are incorporated by reference here in their entirety.

TECHNICAL FIELD

The present invention relates to a medical balloon assembly and in particular to a high strength balloon with asymmetric strengthening.

BACKGROUND ART

Medical balloon assemblies are used for a variety of medical procedures including for the placement of medical devices, such as stents and stent grafts, for angioplasty procedures, for valvuloplasty procedures and so on.

The balloons of such assemblies are typically compliant or non-compliant. Complaint balloons may be made, for example, of polyurethane, Nylon, polyethylene and the like, while non-compliant balloons may be made of polyethylene terephthalate (PET), ultrahigh molecular weight polyethylene such as Dyneema™ and the like.

In order to maximise the wrappability of the balloon for delivery purposes, that it to minimise its folded and wrapped diameter, as well as to maximise its flexibility, the balloon wall is preferably made as thin as possible. This, however, results in a weaker balloon wall with increased chance of rupture of the balloon and limits the pressure to which the balloon can be inflated. Some balloon materials do not gain sufficient strength even with thicker balloon walls.

It is known to provide strengthening elements with such medical balloons, one known example being an embedded sleeve of woven or non-woven fibres in the polymer material forming the balloon. Strengthening elements of this type can provide high strength balloons less likely to tear or burst in use and which can be inflated to higher pressures. While strengthening sleeves can provide such enhancements, they lead to an increase in the overall thickness of the balloon wall and can also lead to an increase in the stiffness of the balloon, particularly when the balloon is deflated and when it is in its wrapped condition.

Examples of medical balloon assemblies having strengthening sleeves are disclosed in U.S.-2008/0033477, U.S.-2004/0082965, U.S.-2002/0098307, U.S.-2006/0085022, U.S.-2007/0219490 and U.S. Pat. No. 6,746,425.

DISCLOSURE OF THE INVENTION

The present invention seeks to provide an improved medical balloon assembly and in particular a high strength balloon with asymmetric strengthening. The balloon assembly could be used for a variety of medical applications including but not limited to: the placement of medical devices, such as stents and stent grafts, angioplasty procedures, valvuloplasty procedures and so on.

According to an aspect of the present invention, there is provided a medical balloon assembly including: an inflatable balloon having at least a body portion and first and second necks at opposing ends of the body portion, the necks being for attachment to a balloon catheter, the body portion having a longitudinal dimension and a circumferential dimension; and a strengthening sleeve extending along at least the body portion of the balloon, the strengthening sleeve including a first set of fibres extending longitudinally along the body portion and a second set of fibres extending circumferentially around the body portion; wherein the fibres of the first set have a lesser thickness than the fibres of the second set.

Preferably, the fibres of the first set have a lower cross-sectional area or volume than the fibres of the second set. In an embodiment, the fibres of the first set are multi-thread fibres with the fibres of the first set preferably having a lower thread count than the fibres of the second set. For example, the fibres of the first set may have a thread count of between 12 and 30 pick/centimeter and the fibres of the second set a thread count of between 20 and 40 pick/centimeter.

The fibres of the first set may have thickness of 0.05 millimeters and the fibres of the second set a thickness of 0.08 millimeters.

In the preferred embodiment, the fibres of the first set, that is the longitudinal fibres, may be of ultrahigh molecular weight polyethylene such as Dyneema having a dtex of 25, or a denier of 23, whereas the fibres of the second set, that is the circumferential or hoop fibres, may be of ultrahigh molecular weight polyethylene such as Dyneema having a dtex of 55, or a denier of 50. The longitudinal and hoop fibres may be made of the same materials, with different pick counts in other embodiments.

The use of longitudinal fibres which are thinner than the circumferential or hoop fibres reduces the thickness of the strengthening element and as a result the overall thickness of the balloon wall. In practice, the longitudinal fibres may not be as strong as the circumferential fibres, in particular may stretch more than the circumferential fibres for a given load. This, though, is not considered disadvantageous and may actually be advantageous in increasing the flexibility of the balloon to bending about the longitudinal direction. Increased flexibility improves trackability of the balloon assembly during endoluminal insertion into a patient's vasculature and also during use.

In some embodiments the fibres of the first set have a first strength and the fibres of the second set have a second strength higher than the strength of the first fibres, whereby the body portion exhibits a lower circumferential extension at inflation pressure than longitudinal extension. The fibres of the first set may have a load to break of 10 Newtons and an e-modulus of 120 GPa, while the fibres of the second set may have a load to break of 18 Newtons and an e-modulus of 107 GPa. The skilled person will appreciate that these are example characteristics.

In an embodiment, the fibres of the first set are made from a more compliant material than the fibres of the second set. In another embodiment the fibres of the first and second sets of fibres are made from the same materials.

Preferably, the fibres of the first and second sets of fibres are made from ultrahigh molecular weight polyethylene or polyester, for example of Dyneema™. In another embodiment the fibres may be made of polyester. As mentioned above, the fibres of the second set may be made of the same materials as the fibres of the first set, though having different characteristics.

The fibres of the first set preferably extend parallel to the longitudinal axis of the body portion, while the fibres of the second set extend perpendicularly to the longitudinal axis of the body portion.

The fibres of the first and second sets may be woven together, in other embodiments they are disposed in overlaying layers.

Advantageously, the first set of fibres extends for substantially the whole length of the balloon. The second set of fibres may be disposed solely on the body portion of the balloon, but could be disposed along a greater extent of the balloon, for example also around conical end sections of the balloon and, if desired, also for the whole length of the balloon.

The balloon assembly can be for any medical application, for example but not limited to: a deployment balloon, an angioplasty balloon or a valvuloplasty balloon.

The teachings herein also cover a balloon catheter assembly including a medical balloon as taught herein.

Other features and advantages of the teachings herein will become apparent from the following description of the preferred embodiments.

BRIEF DESCRIPTION OF THE DRAWINGS

Embodiments of the present invention are described below, by way of example only, with reference to the accompanying drawings, in which:

FIG. 1 is schematic view depicting a balloon catheter assembly which may be structured according to the teachings herein;

FIG. 2 is side elevational view of an example of medical balloon which may be structured according to the teachings herein;

DESCRIPTION OF THE PREFERRED EMBODIMENTS

Figure 3:
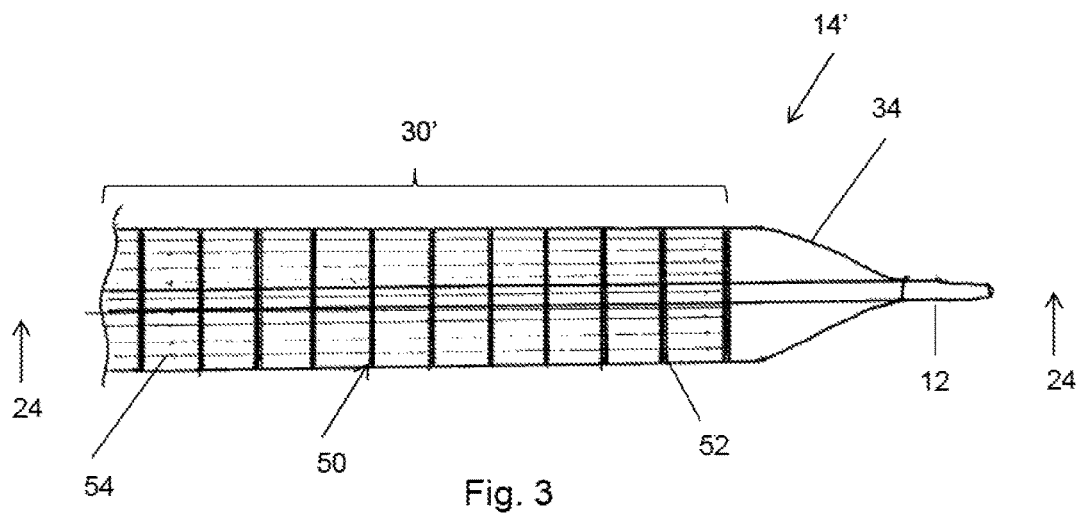
FIG. 3 is a side elevational view of a part of an embodiment of medical balloon.

It is to be understood that the drawings are schematic only and do not show the elements in proportion. The skilled person will readily appreciate the typical dimensions and proportions of the various elements depicted and will also know that these will generally also vary in dependence upon the nature of the vessel in which the device is to be implanted.

Referring first to FIG. 1, this shows in schematic form an example of balloon catheter assembly 10 which can incorporate the structure of strengthened medical balloon as taught herein. The assembly 10 includes a catheter 12 on which an inflatable balloon 14 is disposed and fixed in fluid tight manner. The catheter 12 terminates at a fitting 16, which in this example is a Y-fitting providing a first lumen 18 for the passage of a guide wire through the catheter 12, in known manner, and a second fitting 20 which couples to a lumen within the catheter 12 which itself is coupled to a port (not shown) within the chamber of the balloon 14 for inflating and deflating the balloon 14. An outer sheath 22 is typically provided for covering the balloon 14 when deflated, folded and wrapped around the catheter 12, for deployment into a patient's vasculature.

The balloon 14, as with all embodiments described herein, can be used for any medical application, examples including but not being limited to deployment of a medical device carried on balloon 14, angioplasty procedures and valvuloplasty procedures.

Referring to FIG. 2, this shows in better detail the general structure of the medical balloon 14, in which in this example has a conventional form. Balloon 14 includes a body portion 30 which is generally cylindrical and round in transverse cross-section. At either end of the balloon body portion 30 there are conical end portions 32, 34 which taper towards the catheter 12 and terminate in balloon necks 36, 38 which are sealed to the catheter 12 in fluid tight manner so as to provide a closed chamber 40 within the balloon 14. The catheter 12 typically includes one or more ports within the chamber 40, fluidically coupled to the inflation/deflation lumen of the catheter 12 and to the arm 20 of the Y-fitting 16. The catheter 12 may also be provided with radiopaque marker bands 42, 44 to assist in the visualisation of the balloon 14 during the medical procedure.

It should be appreciated that the balloon 14 could have shapes other than that shown in the example of FIG. 2 and that these are encompassed within the teachings herein.

The balloon 14 has a balloon wall which is preferably made as thin as possible to optimise the foldability and wrappability of the balloon around the catheter 12 for deployment purposes and also for optimising the flexibility of the balloon 14 when wrapped and folded, which improves the trackability of the balloon catheter assembly 10 through the patient's vasculature. The balloon 14, as well as preferably having a thin wall, needs to be sufficiently strong to withstand the conditions through which it is subjected during the medical procedure. It is also often advantageous to be able to increase the working pressure within the balloon 14, for example for angioplasty procedures, for the deployment of stents, stent grafts and so on.

Figure 4:
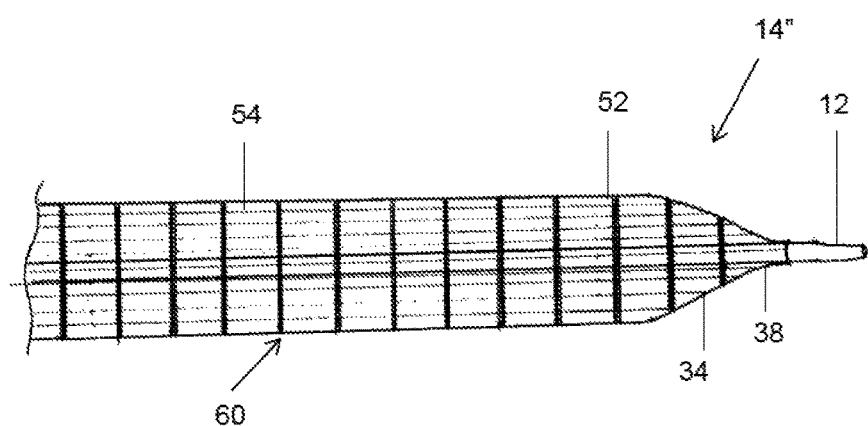
FIG. 4 is a side elevational view of a part of another embodiment of medical balloon.

Referring now to FIGS. 3 and 4, these show different embodiments of strengthening sleeve which can be embedded within the wall of the balloon. The balloon can be made of a variety of materials, including polyamide such as Nylon, polyurethane, polyether block amide such as Pebax™, and so on. The strengthening sleeve 50, 60 of the examples of FIGS. 3 and 4 may be wholly embedded within the thickness of the balloon wall, but in other embodiments may be partially embedded within the balloon wall, or even overlying the balloon wall and advantageously attached thereto.

Referring first to FIG. 3, this shows a strengthening sleeve 50 which is disposed across the body portion 30' of the balloon 14', that is to leave the end cones 32, 34 exposed and free of strengthening sleeve 50. The strengthening sleeve is formed of a first set of longitudinally extending fibres 54 and a second set of circumferentially extending fibres 52. The fibres 52 can be described as circumferential or hoop fibres which in the preferred embodiments extend precisely perpendicularly to the longitudinal axis 24 of the balloon 14' and which are separate from another and spaced relative to one another along the length of the body portion 30'. In some embodiments, the circumferentially extending fibres 52 may be formed as one continuous length of fibre material and disposed helically around the body portion 30. The arrangement shown in FIGS. 3 and 4 is preferred, as providing a structure which can be woven and one which is more stable during inflation in terms of maintaining a stable diameter when the balloon 14' is pressurised.

The fibres 54 of the second set extend parallel to the longitudinal axis 24 of the balloon 14' and are likewise preferably separate fibres which are spaced from one another in the circumferential direction of the body portion 30' of the balloon 14'. The longitudinal and hoop fibres 54, 52 may be intertwined with one another, particularly by weaving, braiding or knitting. They may, however, be on separate layers, with for example, the hoop fibres 52 being disposed within the longitudinal fibres 54, the latter overlying the fibres 52. Other embodiments may have the opposite relationship between the longitudinal fibres 54 and the hoop fibres 52.

In the embodiment of FIGS. 3 and 4 the hoop fibres are shown as being evenly spaced from one another, likewise the longitudinal fibres. In other embodiments, they may be at varying spacing.

The hoop fibres 52 have a greater volume than the longitudinal fibres 54, in some embodiments the hoop fibres 52 are at least twice as thick as the longitudinal fibres 54. The difference in volume is preferably in the form of a difference in the thickness of the hoop and longitudinal fibres 52, 54, with the hoop fibres being at least twice as thick (in the radial direction) than the longitudinal fibres 54. In practice, the fibres 52, 54 may be multi-thread or strand fibres, such that the longitudinal fibres 54 are made of fewer threads or strands than the fibres 52, in the preferred embodiment having about half the number of threads or strands as the hoop fibres 52.

For example, the fibres of the longitudinal fibres 54 may have a thread count of between 20 and 40 pick/centimeter while the hoop fibres 52 have a thread count of between 12 and 30 pick/centimeter.

The longitudinal fibres 54 may have a thickness of 0.05 mm, while the hooped fibres 52 may have a thickness of 0.08 mm.

In a practical embodiment, the longitudinal fibres 54 may be of ultrahigh molecular weight polyethylene such as Dyneema having a dtex of 25, or a denier of 23, whereas the circumferential or hoop fibres 52 may be of ultrahigh molecular weight polyethylene such as Dyneema having a dtex of 55, or a denier of 50. In a practical example, the longitudinal fibres 54 may be made of Dyneema Purity TG dtex25 TS180, whereas the hoop fibres 523 may be made of Dyneema Purity SGX dtex55 TS140.

The longitudinal and hoop fibres 54, 52 may be made of the same materials, in which case the hoop fibres 52 can be expected to have a greater strength than the longitudinal fibres 54.

It can also be expected that the hoop fibres 52 will have a lower coefficient stretch compared to the longitudinal fibres 54. The fibres of the first set may have a load to break of 10 Newtons and an e-modulus of 120 GPa, while the fibres of the second set may have a load to break of 18 Newtons and an e-modulus of 107 GPa. The skilled person will appreciate that these are example characteristics.

In an embodiment, the fibres 52, 54 are made of ultrahigh molecular weight polyethylene, such as Dyneema™, polyester or any other suitable materials. It is not excluded, though, that the fibres 52, 54 may be different, with for example the longitudinal fibres 54 being made of a more compliant material than that from which the fibres 52 are made.

In FIG. 4, the example of strengthening sleeve 60 has a structure very similar to that of the example of FIG. 3 and in particular with circumferential or hoop fibres 52 and longitudinal fibres 54, having the characteristics described above. The primary distinction between the two embodiments of FIGS. 3 and 4 is that the strengthening sleeve 60 of the example of FIG. 4 extends all the way down the conical end portions 32, 34 of the balloon 40", preferably all the way to the necks 36, 38 of the balloon 40". In all other respects, the strengthening sleeve 60 has the same characteristics as the strengthening sleeve 50. It will be appreciated that the strengthening sleeve 50 extends along the entire area of the balloon 14' which in practice will be inflated by inflation fluid.

Figure 5:
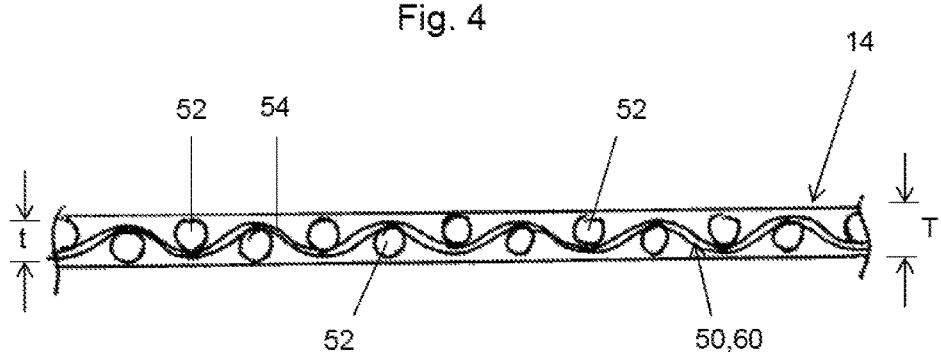
FIG. 5 is a longitudinal cross-sectional view of the balloon wall of an embodiment of medical balloon, showing an embodiment of the structure of the strengthening sleeve.

Referring now to FIG. 5, this shows a cross-sectional view through a portion of the wall of a balloon 14, having the characteristics of all of the embodiments described herein. The example shown in FIG. 5 has the strengthening sleeve 50, 60 entirely embedded within the thickness of a balloon wall although, as explained above, the strengthening sleeve 50, 60 may be partially embedded within the balloon wall (typically exposed at the outer surface of the balloon wall) or may overlay the balloon wall 14. It is preferred that the strengthening sleeve 50, 60 is at least partially embedded within the balloon wall.

The cross-sectional view of FIG. 5 is taken along the longitudinal direction of the balloon 14, such that the hoop fibres 52 extend into and out of the plane of the paper. The longitudinal fibres 54 (of which one can be seen in FIG. 5) extend between the hoop fibres 52 and, in this embodiment are interleaved with the hoop fibres 52 in a woven or braided pattern, but could be knitted in other embodiments. As can be seen in FIG. 5, the circumferential fibres 52 have a much greater cross-sectional area than the longitudinal fibres 54, as explained above, in some embodiments having twice the thickness of the thickness of the longitudinal fibres 54.

The use of longitudinal fibres 54 which are thinner or have lower volume than the circumferential fibres 52 reduces the overall thickness of the strengthening sleeve 50, 60 and as a result enables the overall balloon wall 14 to be made thinner compared to strengthening sleeves which have fibres which have the same thickness circumferential and longitudinal fibres.

The use of thinner longitudinal fibres 54 will theoretically result in the balloon 14 being less resilient to pressure in the longitudinal direction compared to the circumferential direction, in other words that the circumferential or hoop fibres 52 will be the primary fibres for preventing stretching of the balloon wall in the circumferential direction as a result of increased inflation pressure. The circumferential or hoop fibres 52 are, however, the fibres which restrict the circumferential expansion of the balloon 14. Lengthening of the balloon 14 as a result of inflation pressure is a less important characteristic and in any event is controlled by the fact that the balloon 14 is fixed to the balloon catheter 12 at its necks, which will act as an additional stabilisation mechanism for the balloon 14. The fact that the balloon 14 may exhibit greater stretch in the longitudinal direction than in the circumferential direction can also contribute to enhanced longitudinal flexibility of the balloon 14 and assist in deploying the balloon 14 in a curved lumen. Notwithstanding this, the reduction in thickness of the strengthening sleeve 50, 60, as a result of the use of thinner longitudinal fibres 54 is seen as a primary advantage. It will be appreciated that the longitudinal fibres 54 may be made thin enough as in practice to be able to stretch at deployment pressures, whereas it is preferred that the circumferential or hoop fibres 52 do not stretch at such deployment pressures, in order to ensure that the balloon 14 behaves substantially as a non-compliant balloon during its use.

A balloon with a thinner wall has a smaller footprint, or diameter, when folded and wrapped, and improved trackability. The structure is also better suited for use in smaller vessels.

It will be appreciated that the strengthening sleeve may not be needed at the zone of the end cones when these have a greater wall thickness than the balloon body portion, though this option is not excluded.

The longitudinal fibres 54 preferably extend parallel to the longitudinal axis 24 of the balloon 14, although it is not excluded that they may extend at a slight angle to the longitudinal axis 24 but still have their principal direction in the longitudinal axis. Similarly, as explained above, although it is preferred that the circumferential or hoop fibres 52 are perpendicular to the longitudinal axis 24, it is not excluded that in some embodiments they may be at a slight angle to the perpendicular.

When the balloon 14 is used for angioplasty purposes, there may be provided scoring or cutting elements on the outer surface of the balloon 14, typically at the body portion 30 of the balloon. The cutting and scoring elements may be in the form of blades attached to the outside of the balloon 14 or may be polymeric ribs formed integrally with the balloon 14.

The outer surface of the balloon 14 may be smooth, textured, roughened or shaped to suit the medical purpose of the balloon 14.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A medical balloon assembly including:
an inflatable balloon having at least a body portion and first and second necks at opposing ends of the body portion, the necks being for attachment to a balloon catheter, the body portion having a longitudinal dimension and a circumferential dimension; and
a strengthening sleeve extending along at least the body portion of the balloon, the strengthening sleeve including a first set of fibres extending longitudinally along the body portion and a second set of fibres extending circumferentially around the body portion;
wherein the fibres of the first set have a lesser thickness than the fibres of the second set.

2. A medical balloon assembly according to claim 1, wherein the fibres of the first set have a lower cross-sectional area than the fibres of the second set.

3. A medical balloon assembly according to claim 1, wherein the fibres of the first set have a lower thread count than the fibres of the second set.

4. A medical balloon assembly according to claim 3, wherein the fibres of the first set have a thread count of between 20 and 40pick/centimetre and the fibres of the second set have a thread count of between 12 and 30 pick/centimetre.

5. A medical balloon assembly according to claim 1, wherein the fibres of the first set have a first strength and the fibres of the second set have a second strength higher than the strength of the first fibres, whereby the body portion exhibits a lower circumferential extension at inflation pressure than longitudinal extension.

6. A medical balloon assembly according to claim 1, wherein the fibres of the first set have a load to break of 10 Newtons and the fibres of the second set have a load to break of 18 Newtons.

7. A medical balloon assembly according to claim 1, wherein the fibres of the first set are made from a more compliant material than the fibres of the second set.

8. A medical balloon assembly according to claim 1, wherein the fibres of the first and second sets of fibres are made from the same materials.

9. A medical balloon assembly according to claim 8, wherein the fibres of the first and second sets of fibres are made from ultrahigh molecular weight polyethylene or polyester.

10. A medical balloon assembly according to claim 1, wherein the fibres of the first set extend parallel to a longitudinal axis of the body portion and/or wherein the fibres of the second set extend perpendicularly to the longitudinal axis of the body portion.

11. A medical balloon assembly according to claim 1, wherein the fibres of the first and second sets are woven together.

12. A medical balloon assembly according to claim 1, wherein the fibres of the first and second sets are disposed in overlaying layers.

13. A medical balloon according to claim 1, wherein the first set of fibres extends for substantially the whole length of the balloon and wherein the second set of fibres is disposed solely on the body portion of the balloon.

14. A medical balloon according to claim 1, wherein the second set of fibres is disposed around at least a major portion of the balloon.

15. A medical balloon according to claim 1, wherein the balloon is a deployment balloon, an angioplasty balloon or a valvuloplasty balloon.

16. A medical balloon according to claim 1, wherein the second set of fibres is disposed solely on the body portion of the balloon.

17. A medical balloon according to claim 1, wherein the fibres of the second set of fibres are at least twice as thick as the fibres of the first set of fibres.

* * * * *